United States Patent
Saitoh

(10) Patent No.: US 9,176,257 B2
(45) Date of Patent: Nov. 3, 2015

(54) CONJUGATED AROMATIC COMPOUND, OPTICAL MATERIAL, AND OPTICAL ELEMENT

(75) Inventor: Terunobu Saitoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 274 days.

(21) Appl. No.: 13/583,432

(22) PCT Filed: Mar. 14, 2011

(86) PCT No.: PCT/JP2011/056671
§ 371 (c)(1),
(2), (4) Date: Sep. 7, 2012

(87) PCT Pub. No.: WO2011/118541
PCT Pub. Date: Sep. 29, 2011

(65) Prior Publication Data
US 2012/0330052 A1    Dec. 27, 2012

(30) Foreign Application Priority Data

Mar. 23, 2010  (JP) .................................. 2010-066988

(51) Int. Cl.
| | | |
|---|---|---|
| *C07C 69/353* | (2006.01) | |
| *C07C 69/52* | (2006.01) | |
| *C07C 49/788* | (2006.01) | |
| *G02B 1/04* | (2006.01) | |
| *C07C 49/835* | (2006.01) | |
| *C07C 69/54* | (2006.01) | |

(52) U.S. Cl.
CPC ................ *G02B 1/04* (2013.01); *C07C 49/835* (2013.01); *C07C 69/54* (2013.01); *C07C 2102/08* (2013.01)

(58) Field of Classification Search
CPC ...... C07C 49/835; C07C 49/84; C07C 69/54; C07C 2102/10
See application file for complete search history.

(56) References Cited

U.S. PATENT DOCUMENTS 5,286,603 A * 2/1994 Wade et al. ................ 430/281.1

FOREIGN PATENT DOCUMENTS

| CN | 101570643 A | 11/2009 |
|---|---|---|
| DE | 146606 A1 | 2/1981 |
| JP | 2008-158361 A | 7/2008 |
| WO | WO 93/01173 A1 * | 1/1993 |

OTHER PUBLICATIONS

Gao et al, Chinese Chemical Letters, Novel Triphenylamine-based Two-photon Absorption Dyes Including Benzophenone Parts, 2009, 20, pp. 1279-1282.*
Fuson et al, J. Am. Chem. Soc., The Condensation of t-Butylmagnesium Chloride with Duryl o-Isopropenylphenyl Ketone, 1955, 77 (9), pp. 2503-2505.*
Itami et al (Organic Letters, Rapid Construction of Multisubstituted Olefin Structures Using Vinylboronate Ester Platform Leading to Highly Fluorescent Materials, 2004, 6( 22), pp. 4093-4096).*
Wang et al, Journal of Physical Chemistry B, Aggregation Emission Properties of Oligomers Based on Tetraphenylethylene, 2010, 114 (18), pp. 5983-5988.*
"Rapid Construction of MultisubstitutedOlefin Structures Using Vinylboronate Ester Platform Leading to Highly Fluorescent Materials" Itami K et al, organic letters vol. 6, No. 22, pp. 4093-4096.
"The Condensation of t-Butylmagnesium Chloride with Dury o-Isopropenylphenyl Ketone" Peynold Fuson et al, vol. 77, No. 9, pp. 2503-2505, J. Am. Chem. Soc.

* cited by examiner

*Primary Examiner* — Paul A Zucker
(74) *Attorney, Agent, or Firm* — Canon USA, Inc. I.P. Division

(57) ABSTRACT

The present invention relates to a conjugated aromatic compound represented by the Formula (1) in claim 1 (in the formula, $Ar^1$ represents a hydrogen atom or an aryl group optionally having a substituent; $Ar^2$ and $Ar^3$ each represent a hydrogen atom or an aryl group optionally having a substituent but at least one of $Ar^2$ and $Ar^3$ represents an aryl group optionally having a substituent; and A represents an aromatic hydrocarbon group) and relates to an optical material containing the conjugated aromatic compound. The conjugated aromatic compound and the optical material have characteristics of a high chromatic aberration correction function, high refractive-index dispersion characteristics (Abbe number (vd)) and high secondary dispersion characteristics ($\theta g,F$) (anomalous dispersion characteristics).

14 Claims, 2 Drawing Sheets

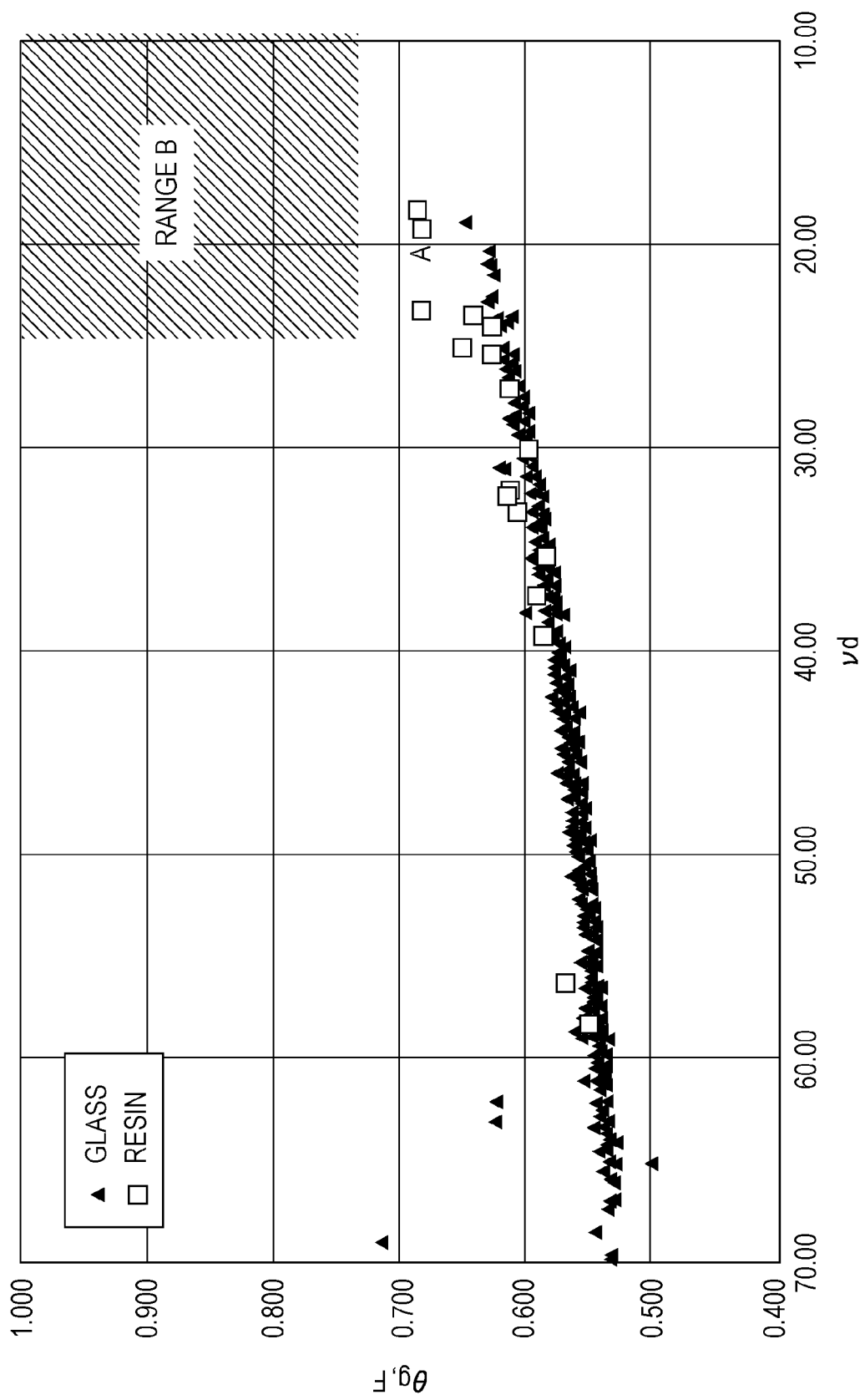

CONJUGATED AROMATIC COMPOUND, OPTICAL MATERIAL, AND OPTICAL ELEMENT

TECHNICAL FIELD

The present invention relates to a conjugated aromatic compound, an optical material, and an optical element formed from the optical material and, more specifically, relates to a conjugated aromatic compound and an optical material having high refractive-index dispersion characteristics (Abbe number (vd)) and high secondary dispersion characteristics (θg,F) (anomalous dispersion characteristics), and relates to an optical element formed from the optical material.

BACKGROUND ART

In general, the refractive index of an optical material, such as a lens material or an organic resin, gradually increases with a decrease in wavelength. As indicators showing this wavelength dispersion of the refractive index, for example, Abbe number (vd) and secondary dispersion characteristics (θg,F) are known. The Abbe number and the θg,F value are specific to each optical material, but many materials have them within a certain range. The secondary dispersion characteristics and Abbe numbers of known optical materials (lens material and organic resins) are shown in FIG. 1. In FIG. 1, ▲ denotes glass, and □ denotes resins.

The Abbe number (vd) and the secondary dispersion characteristics (θg,F) can be represented by the following equations:

Abbe number[$vd$]=($nd$−1)/($nF$−$nC$)

Secondary dispersion characteristics [θg,F]=($ng$−$nF$)/($nF$−$nC$)
($nd$ denotes the refractive index at a wavelength of 587.6 nm; $nF$ denotes the refractive index at a wavelength of 486.1 nm; $nC$ denotes the refractive index at a wavelength of 656.3 nm; and $ng$ denotes the refractive index at a wavelength of 435.8 nm.)

However, optical materials (e.g., lens materials and organic resins) having high θg,F characteristics deviating from the above-mentioned certain range have been synthesized by designing in detail structures (kinds of materials and molecular structures) of the optical materials. For example, polyvinyl carbazole ("A" in FIG. 1), which is an organic resin, has the highest θg,F characteristics in the organic resin materials.

In general, in a refraction optical system, chromatic aberration is decreased by combining lens materials having different dispersion characteristics. For example, in an objective lens of a telescope, the chromatic aberration appearing on the axis is corrected by combining a positive lens element of a low-dispersion lens material and a negative lens element of a high-dispersion lens material. Therefore, when the structure of a lens or the number of lens elements is restricted or when the lens material to be used is limited, it may be very difficult to sufficiently correct chromatic aberration. As one method of solving these problems, optical elements of a glass material having anomalous dispersion characteristics have been designed.

In production of an optical element having, for example, an aspheric surface shape that is excellent in chromatic aberration correction function, for example, formation of an organic resin on spherical surface glass is excellent in mass productivity, moldability, the degree of freedom in shape, and lightness and is therefore advantageous, compared to use of a lens material. However, known organic resins have optical characteristics belonging to the certain range as shown in FIG. 1, and organic resins having discriminating dispersion characteristics are very rare.

Under such background, PTL 1 describes an optical resin composition composed of N-acryloylcarbazole, a multifunctional polyester acrylate, dimethylol tricyclodecane diacrylate, and a polymerization initiator at a predetermined ratio. It is reported that the optical resin composition has good workability and becomes, in its hardened state, a material having sufficient anomalous dispersion characteristics and durability.

On the other hand, the present inventors have focused on the fact that in order to obtain an optical element having a chromatic aberration correction function that is higher than ever, it is significantly effective for optical design that the secondary dispersion characteristics represented by the θg,F value as the material characteristics of an optical element are larger (high θg,F characteristics) so as to deviate from those of general-purpose materials. Specifically, characteristics shown as the range B (vd<25 and θg,F>0.73) in FIG. 1, where the relationship between vd and θg,F deviates from the plots of general-purpose materials, lens materials and organic resins, are significantly effective.

However, currently, there is no material having characteristics (high θg,F) shown as the range B in FIG. 1 and practical utility (low coloring and stability). Note that materials recently provided by Patent Literature 1 all have θg,F values of not larger than 0.70.

CITATION LIST

Patent Literature

PTL 1 Japanese Patent Laid-Open No. 2008-158361

SUMMARY OF INVENTION

The present invention, in view of the above-described background, provides a conjugated aromatic compound and an optical material having characteristics of a high chromatic aberration correction function, high refractive-index dispersion characteristics (Abbe number (vd)) and high secondary dispersion characteristics (θg,F) (high θg,F characteristics). In addition, the present invention provides an optical element formed from the optical material.

The conjugated aromatic compound in the present invention has the following Formula (1):

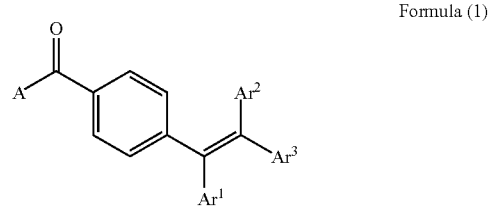

Formula (1)

(in the formula, $Ar^1$ represents a hydrogen atom or an aryl group optionally having a substituent; $Ar^2$ and $Ar^3$ each represent a hydrogen atom or an aryl group optionally having a substituent but at least one of $Ar^2$ and $Ar^3$ represents an aryl group optionally having a substituent; and A represents an aromatic hydrocarbon group).

The optical material according to the present invention contains the conjugated aromatic compound.

The optical element according to the present invention is that molded from the optical material.

Accordingly, the present invention can provide an optical material having characteristics shown as the range B in FIG. 1. By using an optical element molded from the optical material, chromatic aberration can be efficiently eliminated, resulting in reduction in weight and size of an optical system. Note that, hereinafter, the term "high θg,F characteristics" refers to the characteristics shown as the range B in FIG. 1.

Further features of the present invention will become apparent from the following description of exemplary embodiments with reference to the attached drawings.

BRIEF DESCRIPTION OF DRAWINGS

FIG. 1 is a graph showing a relationship between secondary dispersion characteristics and Abbe numbers of commercially available optical materials.

DESCRIPTION OF EMBODIMENT

Figure 2A:
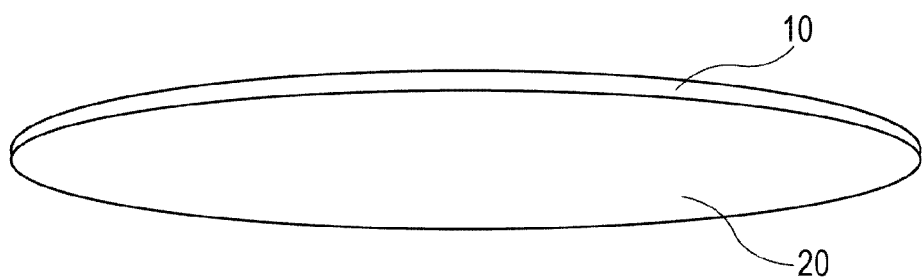
FIG. 2A is a schematic view illustrating an optical element according to the present invention.

The present invention will be described in detail below, but the following description about constitutional elements is an example of embodiment of the present invention, and the present invention is not specified by the contents thereof.

Conjugated Aromatic Compound

The conjugated aromatic compound according to the present invention has the following Formula (1):

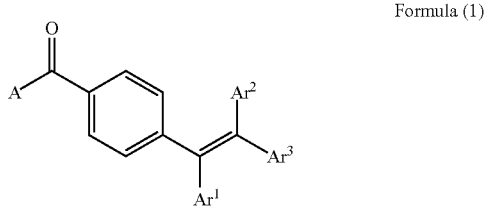

Formula (1)

(in the formula, $Ar^1$ represents a hydrogen atom or an aryl group optionally having a substituent; $Ar^2$ and $Ar^3$ each represent a hydrogen atom or an aryl group optionally having a substituent but at least one of $Ar^2$ and $Ar^3$ represents an aryl group optionally having a substituent; and A represents an aromatic hydrocarbon group).

The present inventors have conducted intensive studies on materials satisfying the characteristics defined by the range B in FIG. 1 and, as a result, have found that a compound having a conjugate structure containing a large number of π electrons and having an adequately long length can be a material having both the characteristics (high θg,F) and practical utility. That is, the compound is a conjugated aromatic compound in which at least one aromatic compound (B) having at least 14 conjugating π electrons binds to an aromatic compound (A) through a sp2 carbon.

Note that, in the present invention, the term "π electron" refers to an electron forming a n bond, and the term "sp2 carbon atom" refers to a carbon atom having two single bonds and one double bond in a planar structure.

In general, since a compound represented by an aromatic compound having a conjugate structure containing a large number of π electrons and having a long length has a band gap smaller than those of general-purpose materials, the absorption edge in the ultraviolet region shifts toward the visual light region side. By the influence thereof, the compound having a conjugate structure containing a large number of π electrons and having a long length has high refractive index characteristics. The effect of the high refractive index characteristics is higher on the short wavelength side, as the inevitable results, the θg,F value is increased to allow the compound to have characteristics belonging to the range B in FIG. 1.

However, a material merely having a conjugate structure containing a large number of π electrons and having a long length cannot to be applied to practical use. In particular, a large aromatic compound (containing a large number of π electrons) has problems in synthesis, compatibility with another compound, and coloring. Furthermore, a non-aromatic compound (e.g., polyene) having a conjugate structure containing a large number of π electrons and having a long length tends to cause, for example, an electrocyclic reaction or a Diels-Alder reaction at room temperature to significantly decrease the storage stability and, therefore, does not have practical utility.

Therefore, the aromatic compound (B) having at least 14 conjugating π electrons can be used. The aromatic compound (B) having at least 14 conjugating π electrons can have at least one benzene ring. Furthermore, the aromatic compound (B) having at least 14 conjugating π electrons can have at least one benzene ring and at least one olefin site. Furthermore, the aromatic compound (B) having at least 14 conjugating π electrons can have at least one benzene ring and one olefin site and can bind to the aromatic compound (A) on the benzene ring through an sp2 carbon atom.

When the number of π electrons is smaller than 14 (for example, biphenyl group), since the successive conjugate structures is small, the characteristics cannot reach the range B in FIG. 1. When the aromatic compound (B) having at least 14 conjugating π electrons binds to the aromatic compound (A) at the olefin site through an sp2 carbon atom, the optical absorption due to conjugation between the olefin site and the sp2 carbon atom is larger than the optical absorption due to conjugation between the benzene ring and the sp2 carbon atom to deteriorate the transmittance, which prevents the use of the compound as an optical material.

Therefore, the aromatic compound (B) having at least 14 conjugating π electrons binds to the aromatic compound (A) on the benzene ring through an sp2 carbon atom.

A compound having a conjugate structure containing a large number of π electrons and having a long length, such as polyacetylene or polythiophene, may have a color. Therefore, the compound having a conjugate structure containing a large number of π electrons is controlled to have an adequate length.

In order to obtain a conjugate structure containing a large number of π electrons and having an adequate length, the aromatic compound (A) is bound to the aromatic compound (B) having at least 14 conjugating π electrons through an sp2 carbon atom. This is because that the plane of the aromatic compound (A) and the plane of the sp2 carbon atom are twisted from the same plane by the steric repulsion between a substituent in the aromatic compound (A) and the substituent on the sp2 carbon atom to make the conjugate structure of the aromatic compound (A) and the conjugate structure of the aromatic compound (B) having at least 14 conjugating π electrons, which includes the sp2 carbon atom, to have adequate lengths, which allows the material to have high θg,F characteristics and practical utility. The conjugate structure having an adequate length can be also improved in practical utility, such as storage stability for an electrocyclic reaction, a Diels-Alder reaction, etc., compatibility, and coloring.

For these reasons, a conjugated aromatic compound in which the aromatic compound (B) having at least 14 conjugating π electrons binds to the aromatic compound (A) through an sp2 carbon atom can solve the above-mentioned problems. This is also supported by the simulation results through discrete Fourier transform.

The conjugated aromatic compound shown by Formula (1) of the present invention is a conjugated aromatic compound in which an aromatic hydrocarbon group A, which corresponds to the aromatic compound (A), and a group of an aromatic compound having at least 14 conjugating n electrons, which corresponds to the aromatic compound (B), are bonded to each other through an sp2 carbon atom.

The group of the aromatic compound (B) having at least 14 conjugating π electrons in Formula (1) is a group having a structure represented by the following Formula (5):

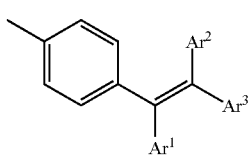

Formula (5)

$Ar^1$ represents a hydrogen atom or an aryl group optionally having a substituent; and $Ar^2$ and $Ar^3$ each represent a hydrogen atom or an aryl group optionally having a substituent but at least one of $Ar^2$ and $Ar^3$ represents an aryl group optionally having a substituent.

In the group having a structure represented by Formula (5), $Ar^1$ can be a hydrogen atom, and $Ar^2$ and $Ar^3$ can each represent a hydrogen atom or an aryl group optionally having a substituent but at least one of $Ar^2$ and $Ar^3$ represents an aryl group optionally having a substituent; or $Ar^1$ can be a hydrogen atom, and $Ar^2$ and $Ar^3$ can be aryl groups, from the viewpoints of easiness of synthesis or acquisition of raw materials and characteristics.

Examples of the aryl group optionally having a substituent include phenyl groups, naphthyl groups, anthracenyl groups, 4-methylphenyl groups, 4-methoxyphenyl groups, 4-chlorophenyl groups, 4-fluorophenyl groups, 4-bromophenyl groups, 4-iodophenyl groups, 4-dimethylaminophenyl groups, 4-vinylphenyl groups, 4-allylphenyl groups, 2-methylphenyl groups, 2-methoxyphenyl groups, 2-dimethylaminophenyl groups, 4-nitrophenyl groups, 2-vinylphenyl groups, and 2-allylphenyl groups, but are not limited thereto. The aryl group can be a phenyl group from the viewpoints of easiness of synthesis or acquisition of raw materials and characteristics.

"A" in Formula (1) represents an aromatic hydrocarbon group. The aromatic hydrocarbon group A is not particularly limited as long as it is an aromatic compound, and examples thereof include those having benzene as their main skeletons, those having naphthalene as their main skeletons, those having anthracene as their main skeletons, those having fluorene as their main skeletons, those having biphenyl as their main skeletons, those having diaryl ether as their main skeletons, those having diaryl sulfide as their main skeletons, those having binaphthalene as their main skeletons, those having pyridine as their main skeletons, those having carbazole as their main skeletons, those having thianthrene as their main skeletons, those having dibenzodioxane as their main skeletons, those having benzofuran as their main skeletons, those having acenaphthylene as their main skeletons, those having acridine as their main skeletons, those having benzothiazole as their main skeletons, those having quinoline as their main skeletons, those having isoquinoline as their main skeletons, those having pyrene as their main skeletons, those having indazole as their main skeletons, those having indole as their main skeletons, those having indane as their main skeletons, those having indene as their main skeletons, those having benzoquinoline as their main skeletons, those having benzoxazole as their main skeletons, those having biquinoline as their main skeletons, those having phenanthrene as their main skeletons, those having phenanthroline as their main skeletons, those having bifluorenylidene as their main skeletons, those having ferrocene as their main skeletons, those having phenoxathiin as their main skeletons, those having dibenzothiophene as their main skeletons, and those having dibenzofuran as their main skeletons. The aromatic hydrocarbon group A can be those having benzene as their main skeletons and those having naphthalene as the main skeletons, from the viewpoints of easiness of synthesis, characteristics, coloring, and so on.

The aromatic hydrocarbon group having naphthalene as its main skeleton can have a structure represented by the following Formula (2):

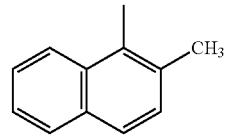

Formula (2)

The aromatic hydrocarbon group having benzene as its main skeleton can have a structure represented by the following Formula (3):

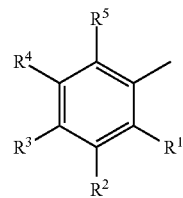

Formula (3)

(in the formula, $R^1$ to $R^5$ each independently represent Y, a hydrogen atom, an alkyl group having 1 to 4 carbon atoms, or an aryl group optionally having a substituent, wherein Y represents a hydroxyl group or a group having a structure represented by the following Formula (4):

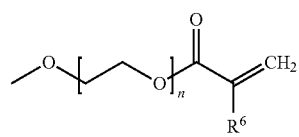

Formula (4)

$R^6$ represents a hydrogen atom or a methyl group; and n is 0 or 1).

Examples of the alkyl group having 1 to 4 carbon atoms include a methyl group, an ethyl group, a propyl group, an i-propyl group, a butyl group, an i-butyl group, and a t-butyl group.

Examples of the aryl group optionally having a substituent include phenyl groups, naphthyl groups, anthracenyl groups, 4-methylphenyl groups, 4-methoxyphenyl groups, 4-chlorophenyl groups, 4-fluorophenyl groups, 4-bromophenyl groups, 4-iodophenyl groups, 4-dimethylaminophenyl groups, 2-methylphenyl groups, 2-methoxyphenyl groups, 2-dimethylaminophenyl groups, and 4-nitrophenyl groups, but are not limited thereto.

Furthermore, from the viewpoints of easiness of synthesis, characteristics, coloring, and so on, $R^1$ to $R^5$ in Formula (3) can be as follows: $R^1$ and $R^5$ are methyl groups, and $R^2$, $R^3$, and $R^4$ are hydrogen atoms; $R^1$, $R^3$, and $R^5$ are methyl groups, and $R^2$ and $R^4$ are hydrogen atoms; $R^1$ is a methyl group, and $R^2$, $R^3$, $R^4$, and $R^5$ are hydrogen atoms; $R^1$, $R^3$, and $R^4$ are methyl groups, and $R^2$ and $R^5$ are hydrogen atoms; $R^1$ and $R^2$ are methyl groups, and $R^3$, $R^4$, and $R^5$ are hydrogen atoms; $R^1$ is an isopropyl group, and $R^2$, $R^3$, $R^4$, and $R^5$ are hydrogen atoms; $R^1$ and $R^3$ are each Y, and $R^2$, $R^4$, and $R^5$ are hydrogen atoms; $R^1$ and $R^2$ are each Y, and $R^3$, $R^4$, and $R^5$ are hydrogen atoms; $R^1$ is Y, and $R^2$, $R^3$, $R^4$, and $R^5$ are hydrogen atoms; $R^1$ is Y, $R^2$, $R^3$, and $R^5$ are hydrogen atoms, and $R^4$ is a methyl group; $R^1$ and $R^5$ are methyl groups, $R^2$ and $R^4$ are hydrogen atoms, and $R^3$ is Y; $R^1$ is Y, $R^2$ and $R^4$ are tert-butyl groups, and $R^3$ and $R^5$ are hydrogen atoms; $R^1$, $R^3$, and $R^5$ are each Y, and $R^2$ and $R^4$ are hydrogen atoms; $R^1$, $R^2$, and $R^3$ are each Y, and $R^4$ and $R^5$ are hydrogen atoms; $R^1$ is Y, $R^2$ is a methyl group, and $R^3$, $R^4$, and $R^5$ are hydrogen atoms; $R^1$ is Y, $R^2$ is X, and $R^3$, $R^4$, and $R^5$ are hydrogen atoms; or $R^1$ is Y, $R^2$ is X, $R^3$ and $R^5$ are hydrogen atoms, and $R^4$ is a methyl group. X shows the position at which a second or subsequent structure represented by Formula (1) binds to the anterior structure when a molecule has two or more structures represented by Formula (1) in the molecule. Y represents a hydroxyl group or a group having a structure represented by Formula (4).

Furthermore, from the viewpoints of easiness of synthesis, characteristics, coloring, and so on, $R^1$ to $R^5$ in Formula (3) can be as follows: $R^1$ and $R^5$ are methyl groups, and $R^2$, $R^3$, and $R^4$ are hydrogen atoms; $R^1$, $R^3$, and $R^5$ are methyl groups, and $R^2$ and $R^4$ are hydrogen atoms; $R^1$ is a methyl group, and $R^2$, $R^3$, $R^4$, and $R^5$ are hydrogen atoms; $R^1$ and $R^3$ are each Y, and $R^2$, $R^4$, and $R^5$ are hydrogen atoms; $R^1$ is Y, and $R^2$, $R^3$, $R^4$, and $R^5$ are hydrogen atoms; $R^1$ is Y, $R^2$, $R^3$, and $R^5$ are hydrogen atoms, and $R^4$ is a methyl group; $R^1$ and $R^5$ are methyl groups, $R^2$ and $R^4$ are hydrogen atoms, and $R^3$ is Y; or $R^1$ is Y, $R^2$ is X, and $R^3$ and $R^5$ are hydrogen atoms, and $R^4$ is a methyl group, wherein X shows the position at which the compound binds to the sp2 carbon atom; and Y represents a hydroxyl group or a group having a structure represented by Formula (4).

Process of Producing Conjugated Aromatic Compound

An example of the process of producing the conjugated aromatic compound of the present invention will now be described.

The conjugated aromatic compound of the present invention is not particularly limited by the production route thereof and may be produced by any process. For example, a process using, as raw materials, an aldehyde compound of the aromatic compound (A) constituting the aromatic hydrocarbon group A and an aromatic compound (B) having at least 14 conjugating π electrons constituting the group having a structure represented by Formula (5) can produce a conjugated aromatic compound without using any specific reaction. In this process, an organometallic species of the aromatic compound (B) having at least 14 conjugating π electrons is prepared, followed by a reaction with the aldehyde compound of the aromatic compound (A) to obtain an alcohol, and subsequent oxidation gives a conjugated aromatic compound. On this occasion, when the raw material has a substituent that is unstable under the above-mentioned reaction conditions, the reaction can be performed by protecting the substituent. When the raw material has a hydroxyl group, the hydroxyl group is protected with a protecting group before the reaction, and, after deprotection, a necessary number of (meth)acrylation is performed to obtain a conjugated aromatic compound.

The aldehyde compound can be produced by any known process without particular limitation. For example, a process using a transition metal or a process preparing an organometallic species and subjecting it to a reaction with N,N-dimethylformamide can be employed.

The organometallic species is not particularly limited as long as it is nucleophilic to react with aldehyde, and is, for example, a lithium species or a magnesium species. The lithium species can be prepared by letting, for example, butyllithium or t-butyllithium act on a compound represented by Formula (5) having a brominated bond. The magnesium species can be prepared by letting, for example, magnesium or isopropyl magnesium bromide act on the compound. The organometallic species can be prepared under any known conditions without particular limitation. For example, dehydrated tetrahydropyran or an ether-type solvent, such as diethyl ether, can be used for preparing the organometallic species. In such a case, the lithium species can be prepared at a low temperature.

The resulting alcohol can be oxidized by any known method without particular limitation. Examples of the oxidizing agent include ozone, hydrogen peroxide, potassium permanganate, potassium chlorate, potassium dichromate, sodium bromate, halogens, osmium teroxide, manganese dioxide, DMSO, a Dess-Martin reagent, peracetic acid, mCPBA, chromic acid, lead oxides, and TPAP, but are not limited thereto. However, when a peroxide is used, it is necessary to avoid epoxydation of the olefin site.

The protecting group for the hydroxyl group is not particularly limited as long as it is suitable for the conditions, and examples thereof include silyl protecting groups such as a methoxymethyl group, a tetrahydropyranyl group, and a trimethylsilyl group. The protection and deprotection can be each performed by any known methods.

The (meth)acrylation can be performed by an appropriately selected method. Typical methods thereof are, for example, esterification of a hydroxyl group with (meth)acrylate halide or (meth)acrylic acid anhydride; an ester-exchange reaction using an ester of a lower alcohol of (meth)acrylic acid; and direct esterification by dehydration condensation of (meth)acrylic acid and a diol using a dehydration-condensation agent such as N,N'-dicyclohexycarbodiimide.

When the conjugated aromatic compound of the present invention has a (meth)acrylate group, in order to prevent polymerization during reaction or storage, a polymerization inhibitor may be used as needed. Examples of the polymerization inhibitor include hydroquinones such as p-benzoquinone, hydroquinone, hydroquinone monomethyl ether, 2,5-diphenyl-para-benzoquinone; N-oxyradicals such as tetramethylpiperidinyl-N-oxyradical (TEMPO); substituted catechols such as t-butyl catechol; amines such as phenothiazine, diphenylamine, and phenyl-β-naphthylamine; and nitrosobenzene, picric acid, molecular oxygen, sulfur, and copper(II) chloride. Among them, from the viewpoint of general-purpose and inhibition of polymerization, hydroquinones, phenothiazine, and N-oxyradicals, in particular, hydroquinones, can be used.

The amount of the polymerization inhibitor is usually at least 10 ppm and preferably 50 ppm or more based on the conjugated aromatic compound and is usually at most 10000 ppm and preferably 1000 ppm or less. If the amount is too small, the effect as a polymerization inhibitor is not expressed or insufficient, which causes a risk of polymerization during the reaction or during concentration in the post-treatment process. If the amount is too large, for example, the inhibitor has a risk of acting as an impurity when an optical material, described below, is produced or causing disadvantageous effects such as inhibition of polymerization.

Optical Material

An optical material according to the present invention will now be described.

The optical material of the present invention is a composition composed of the above-described conjugated aromatic compound, a polymerization initiator, and, as needed, a photosensitizer, and a resin.

If the content of the conjugated aromatic compound contained in the optical material of the present invention is too small, the optical characteristics may not reach the range B, and therefore the content is 10% by weight or more and preferably from 50 to 99% by weight.

Examples of the polymerization initiator include those that generate radical species or cation species by light irradiation and those that generate radical species by heat, but are not limited thereto.

Examples of the polymerization initiator that generates a radical species by light irradiation include 2-benzyl-2-dimethylamino-1-(4-morpholinophenyl)-1-butanone, 1-hydroxy-cyclohexyl-phenylketone, 2-hydroxy-2-methyl-1-phenyl-propan-1-on, bis(2,4,6-trimethylbenzoyl)-phenylphosphine oxide, 4-phenylbenzophenone, 4-phenoxybenzophenone, 4,4'-diphenylbenzophenone, and 4,4'-diphenoxybenzophenone, but are not limited thereto. Examples of the polymerization initiator that generates a cation species by light irradiation include iodonium (4-methylphenyl)[4-(2-methylpropyl)phenyl]-hexafluorophosphate, but are not limited thereto.

Examples of the polymerization initiator that generates a radical species by heat include azo compounds such as azobisisobutyronitrile (AIBN) and peroxides such as benzoyl peroxide, t-butylperoxypyvalate, t-butylperoxyneohexanoate, t-hexylperoxyneohexanoate, t-butylperoxyneodecanoate, t-hexylperoxyneodecanoate, cumylperoxyneohexanoate, and cumylperoxyneodecanoate, but are not limited thereto.

When polymerization is initiated by irradiation with light, for example, ultraviolet rays, a known sensitizer can be used. Typical examples of the sensitizer include benzophenone, 4,4-diethylaminobenzophenone, 1-hydroxycyclohexyl phenylketone, p-dimethylaminobenzoic acid isoamyl, 4-dimethylaminobenzoic acid methyl, benzoin, benzoin ethyl ether, benzoin isobutyl ether, benzoin isopropyl ether, 2,2-diethoxyacetophenone, o-benzoylbenzoic acid methyl, 2-hydroxy-2-methyl-1-phenylpropan-1-on, and acylphosphine oxide.

The addition ratio of a photoinitiator to a polymerizable resin component can be appropriately selected depending on light quantity and also additional heating temperature, and also can be adjusted depending on the target average molecular weight of a resulting polymer.

The amount of the photoinitiator used in hardening or molding of the optical material of the present invention can be in the range of 0.01 to 10.00% by weight based on the polymerizable component. A single photoinitiator or a combination of photoinitiators can be used depending on the reactivity of a resin and the wavelength of irradiation light.

The generic resin that can be used is not particularly limited, and examples thereof include (meth)acrylate compounds, e.g., 1,3-adamantanediol dimethacrylate, 1,3-adamantanedimethanol dimethacrylate, tricyclodecane dimethanol diacrylate, pentaerythritol tetraacrylate, propoxylated neopentyl glycol diacrylate, dipropylene glycol diacrylate, ethoxylated bisphenol A dimethacrylate, tris(2-hydroxyethyl)isocyanurate triacrylate, 2(2-ethoxyethoxy)ethyl acrylate, stearyl acrylate, tetrahydrofurfuryl acrylate, 2-phenoxyethyl acrylate, isodecyl acrylate, isobonyl acrylate, isobonyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylolpropane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenylmethacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4-acryloxyethoxyphenyl)sulfone, 1,1-bis(4-methacryloxyethoxyphenyl)sulfone, 1,1-bis(4-acryloxydiethoxyphenyl)sulfone, 1,1-bis(4-methacryloxydiethoxyphenyl)sulfone, dimethylol tricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methylthio acrylate, methylthio methacrylate, phenylthio acrylate, benzylthio methacrylate, xylylenedithiol diacrylate, xylylenedithiol dimethacrylate, mercaptoethyl sulfide diacrylate, and mercaptoethyl sulfide dimethacrylate; allyl compounds, e.g., allylglycidyl ether, diallylphthalate, diallylterephthalate, diallylisophthalate, diallylcarbonate, and diethylene glycol bisallylcarbonate; vinyl compounds, e.g., styrene, chlorostyrene, methylstyrene, bromostyrene, dibromostyrene, divinylbenzene, and 3,9-divinylspirobi(m-dioxane); and diisopropenylbenzene, but the resin is not limited thereto.

The generic resin may be a thermoplastic resin, and examples thereof include polyolefin resins, e.g., ethylene homopolymers, random or block copolymers of ethylene and one or more α-olefins such as propylene, 1-butene, 1-pentene, 1-hexene, and 4-methyl-1-pentene, random or block copolymers of ethylene and one or more of vinyl acetate, acrylic acid, methacrylic acid, methyl acrylate, and methyl methacrylate, propylene homopolymers, random or block copolymers of propylene and one or more α-olefins other than propylene, such as 1-butene, 1-pentene, 1-hexene, and 4-methyl-1-pentene, 1-butene homopolymers, ionomer resins, and mixtures of these polymers; hydrocarbon base resins such as petroleum resins and terpene resins; polyester resins such as polyethylene terephthalate, polybutylene terephthalate, and polyethylene naphthalate; polyamide resins such as Nylon 6, Nylon 66, Nylon 11, Nylon 12, Nylon 610, Nylon 6/66, Nylon 66/610, and Nylon MXD; acrylic resins such as polymethyl methacrylate; styrene or acrylonitrile base resins such as polystyrene, styrene-acrylonitrile copolymers, styrene-acrylonitrile-butadiene copolymers, and polyacrylonitrile; polyvinyl alcohol resins such as polyvinyl alcohol, ethylene-vinyl alcohol copolymers; polycarbonate resins; polyketone resins; polymethylene oxide resins; polysulfone resins; polyimide resins; and polyamideimide resins. These can be used alone or as a mixture of two or more thereof.

When the amount of the resin contained in the optical material of the present invention is too small, the long term stability of molded products may be decreased. Therefore, the amount is 1% by weight or more and preferably 20 to 90% by weight.

Process of Forming Molded Product (Optical Material)

In a process of forming a molded product of an optical material of the present invention, for example, a thin-layer structure is formed on a substrate made of a light-transmitting material through molding by disposing a metal mold on a glass substrate, pouring a fluid of an optical material or an optical resin composition between them, and lightly pressing them. While maintaining this state, the optical material or the optical resin composition is polymerized. The light irradiation for the polymerization is conducted with light having an appropriate wavelength corresponding to the mechanism caused by radical generation using a photoinitiator, usually, ultraviolet or visible light. For example, the molded raw material, such as a monomer, for preparing an optical material is uniformly irradiated with light through the light-transmitting material used as the substrate, specifically, the glass substrate. The light quantity to be irradiated is appropriately selected according to the mechanism caused by radical generation using a photoinitiator or according to the content ratio of the photoinitiator.

In production of molded product of the optical material by such photopolymerization, in order to uniformly irradiate the whole molded raw material, such as a monomer, with irradiation light, the wavelength of the irradiation light is selected such that uniform irradiation through the optical-transmitting material serving as the substrate, for example, a glass substrate, is possible. On this occasion, the total thickness of the molded product of the optical material formed on the substrate of an optical-transmitting material can be reduced by means of the present invention.

Similarly, a molded product can be produced by thermal polymerization. In this case, a more uniform temperature of the whole molded raw material can be maintained, and the total thickness of the molded product of the polymerizable composition formed on the substrate of an optical-transmitting material can be reduced by means of the present invention. In order to form a molded product of an optical material having a large total thickness, it is necessary to select the irradiation quantity, the irradiation intensity, the light source, etc. with further consideration for film thickness, absorption of the resin component, and absorption of fine particle component.

The process of forming the molded product of a mixture composition with the thermoplastic resin is not particularly limited. A molded product having excellent characteristics, such as low birefringence and high mechanical strength and dimensional accuracy, can be obtained by melt molding. Examples of the melt molding include pressing, extrusion, and injection molding. The injection molding can be used from the viewpoint of moldability and productivity. The molding conditions for the molding process are appropriately selected according to the application purpose or the molding method, but the temperature of the resin composition in injection molding is preferably in the range of 150 to 400° C., more preferably in the range of 200 to 350° C., and most preferably in the range of 200 to 330° C. By molding in the above-mentioned temperature range, the resin can be provided with appropriate fluidity during the molding to prevent occurrence of shrinkage and distortion, to prevent of occurrence of silver streak due to thermal decomposition of the resin, and to effectively prevent yellowing of the molded product.

FIG. 2A is a schematic view illustrating the thus-produced optical element. The reference number 10 in the figure denotes an optical member made of the above-described molded product, and the reference number 20 denotes a glass lens substrate.

An optical element having an optical material disposed between glass lenses can be obtained by using an optical material unified with a glass lens substrate and another glass lens substrate, as needed. For example, an optical element having an optical material disposed between glass lenses can be obtained by pouring an optical material between glass lenses disposed so as to face each other with the optical material surface sides therebetween, lightly pressing them, and, while maintaining this state, optically polymerizing the optical material.

Figure 2B:
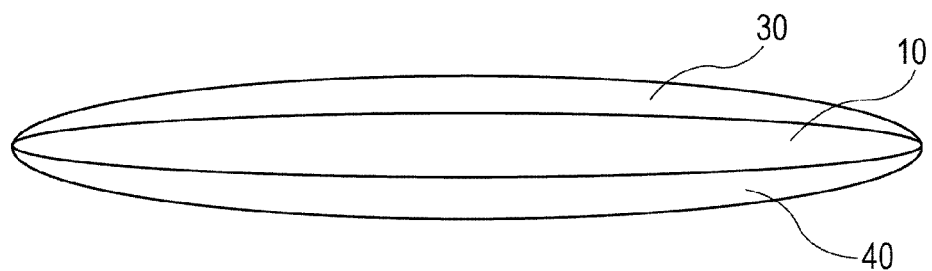
FIG. 2B is a schematic view illustrating an optical element according to the present invention.

FIG. 2B is a schematic view illustrating the thus-produced optical element. The reference number 10 in the figure denotes an optical member made of the above-described molded product, and the reference numbers 30 and 40 denote glass lens substrates.

The molded product formed by molding the optical material of the present invention by the above-described method can be used as an optical element. Examples of the optical element include camera lenses.

Example 1

The present invention will be described in more detail with reference to examples, but is not limited to the following examples unless it is beyond its gist. Note that synthesized products were analyzed with JNM-ECA400 NMR, a product of JEOL Ltd.

Synthesis Example 1

Synthesis process of 2-(4-bromo-3,5-dimethylphenoxy)tetrahydropyran

Pyridinium para-toluenesulfonate (0.01 g) was added to a chloroform solution containing 4-bromo-3,5-dimethylphenol (50 g) and 3,4-dihydro-2H-pyran (35 g), followed by stirring. After confirmation of the degree of reaction progress by thin-layer chromatography (hereinafter referred to as TLC), the reaction was quenched with triethylamine. The organic phase was washed with water and saturated brine in this order. The resulting organic phase was dried over anhydrous magnesium sulfate. Subsequently, the organic phase was concentrated and purified by column chromatography to obtain 70 g (yield: 980) of 2-(4-bromo-3,5-dimethylphenoxy)tetrahydropyran as a colorless liquid.

A tetrahydrofuran solution (40 mL) of 2-(4-bromo-3,5-dimethylphenoxy)tetrahydropyran (4.8 g) synthesized in Synthesis Example 1 was cooled to −78° C., and n-butyllithium (2.6 M, 7.2 mL) was gradually dropped therein. The resulting mixture was stirred at the same temperature for 2 hours. After addition of 4-(2,2-diphenyl-1-vinyl)-benzaldehyde (4.0 g), the mixture was stirred for 12 hours while warming to room temperature. After confirmation of the degree of reaction progress by TLC, the reaction was quenched with an aqueous solution of ammonium chloride, and the organic phase was extracted with ethyl acetate.

The resulting organic phase was dried over anhydrous magnesium sulfate. Subsequently, the organic phase was concentrated and purified by column chromatography. To a chloroform solution of the resulting product, manganese dioxide (15 g) was added. The mixture was stirred at room temperature for 24 hours. After confirmation of the degree of reaction progress by TLC, the manganese dioxide was removed by filtration, and the solvent was concentrated to obtain a concentrate.

To a tetrahydrofuran solution (50 mL) of this concentrate, a 6 N hydrochloric acid solution (1 mL) was added. The mixture was stirred at room temperature for 12 hours. After confirmation of the degree of reaction progress by TLC, the reaction was quenched with an aqueous solution of sodium hydrogen carbonate, and the organic phase was extracted with ethyl acetate. The resulting organic phase was dried over anhydrous magnesium sulfate, concentrated, and purified by column chromatography to obtain 5.0 g (yield: 73%) of [4-(2,2-diphenyl vinyl)phenyl]-(4-hydroxy-2,6-dimethylphenyl)methane (1) as a light yellow liquid. The structure of Product 1 was confirmed by 1H-NMR. Table 1 shows optical characteristics and practical utility of Product 1.
Product 1
$^1$H-NMR (CDCl3; TMS): δ 2.02 (s, 3H), 2.05 (s, 6H), 6.61 (br, 1H), 6.79 (s, 2H), 6.98 (s, 1H), 7.06-7.33 (m, 12H), 7.56 (d, 2H)

Example 2

A chloroform solution (150 mL) of the compound (16.5 g) synthesized in Example 1 was cooled to 0° C. Chloride methacrylate (6.5 g) and triethylamine (12 g) were successively dropped into the chloroform solution, and the resulting mixture was stirred for 2 hours while warming to 25° C. After confirmation of the degree of reaction progress by TLC, the reaction was quenched with an aqueous solution of sodium hydrogen carbonate. The organic phase was extracted with ethyl acetate, and the resulting organic phase was washed with a 0.5 N aqueous solution of sodium hydroxide.

The resulting organic phase was dried over anhydrous magnesium sulfate, concentrated, and purified by column chromatography to obtain 4.4 g (yield: 58%) of 4-[4-(2,2-diphenylvinyl)benzoyl]-3,5-dimethylphenyl methacrylate (2) as a light yellow solid. The structure of Product 2 was confirmed by 1H-NMR. Table 1 shows optical characteristics and practical utility of Product 2.
Product 2
$^1$H-NMR (CDCl3; TMS): δ 2.04 (s, 3H), 2.09 (s, 6H), 5.76 (s, 1H), 6.35 (s, 1H), 6.84 (s, 2H), 6.99 (s, 1H), 7.06-7.35 (m, 12H), 7.56 (d, 2H)

Example 3

4-[4-(2,2-Diphenylvinyl)-benzoyl]-3,5-dimethylphenyl acrylate (3) (4.3 g, yield: 52%) was obtained as a light yellow solid by the same method as in Example 2 except that chloride acrylate (6.0 g) was used instead of chloride methacrylate (6.5 g). The structure of Product 3 was confirmed by 1H-NMR. Table 1 shows optical characteristics and practical utility of Product 3.
Product 3
$^1$H-NMR (CDCl3; TMS): δ 2.25 (s, 6H), 5.79 (d, 1H), 6.42 (d, 1H), 6.51 (dd, 1H), 6.98 (s, 1H), 7.01 (s, 2H), 7.06-7.35 (m, 14H)

Example 4

Product 1 (0.3 g) synthesized in Example 1 was added to a N,N-dimethylformamide solution (10 mL) containing 0.03 g of sodium hydride (55%) at 0° C., and the mixture was stirred at the same temperature for 1 hour. To the mixture, 2-(2-bromoethoxy)tetrahydro-2H-pyran (0.14 g) was added. The mixture was stirred for 12 hours while warming to 25° C. After confirmation of the degree of reaction progress by TLC, the reaction was quenched with an aqueous solution of ammonium chloride. The organic phase was extracted with ethyl acetate. The resulting organic phase was concentrated and was dissolved in tetrahydrofuran to obtain a solution (10 mL) thereof, followed by addition of a 6 N aqueous solution of hydrochloric acid (0.5 mL). The resulting mixture was stirred at 25° C. for 12 hours. After confirmation of the degree of reaction progress by TLC, the reaction was quenched with an aqueous solution of sodium hydrogen carbonate. The organic phase was extracted with ethyl acetate, and the resulting organic phase was concentrated and purified by column chromatography to obtain an intermediate compound.

2-{4-[4-(2,2-Diphenylvinyl)benzoyl]-3,5-dimethylphenoxy}ethyl methacrylate (4) (0.34 g, yield: 68%) was obtained as a light yellow liquid by the same method as in Example 2 except that the intermediate compound (0.40 g) was used instead of the compound (13 g) synthesized in Example 1 and that the amount of chloride methacrylate was changed to 0.14 g instead of 6.5 g, and the amount of triethylamine was changed to 0.18 g instead of 12 g. The structure of Product 4 was confirmed by 1H-NMR. Table 1 shows optical characteristics and practical utility of Product 4.
Product 4
$^1$H-NMR (CDCl3; TMS): δ 1.83 (s, 3H), 2.22 (s, 6H), 3.81-3.93 (m, 2H), 4.13-4.22 (m, 2H), 5.64 (d, 1H), 6.12 (d, 1H), 6.83 (s, 2H), 6.98 (s, 1H), 7.26-7.65 (m, 14H)

Example 5

Product 2 (0.3 g) synthesized in Example 2 was added to a tetrahydrofuran solution (10 mL) containing 0.03 g of sodium hydride (55%) at 0° C., and the mixture was stirred at the same temperature for 1 hour. To the mixture, 2-(2-bromoethoxy)tetrahydro-2H-pyran (0.14 g) was added. The mixture was stirred for 12 hours while warming to 25° C. After confirmation of the degree of reaction progress by TLC, the reaction was quenched with an aqueous solution of ammonium chloride. The organic phase was extracted with ethyl acetate. The resulting organic phase was concentrated and was dissolved in tetrahydrofuran to obtain a solution (10 mL) thereof, followed by addition of a 6 N aqueous solution of hydrochloric acid (0.5 mL). The resulting mixture was stirred at 25° C. for 12 hours. After confirmation of the degree of reaction progress by TLC, the reaction was quenched with an aqueous solution of sodium hydrogen carbonate. The organic phase was extracted with ethyl acetate, and the resulting organic phase was concentrated and purified by column chromatography to obtain an intermediate compound.

2-{4-[4-(2,2-Diphenylvinyl)benzoyl]-3,5-dimethylphenoxy}ethyl acrylate (5) (0.29 g, yield: 58%) was obtained as a light yellow liquid by the same method as in Example 2 except that the intermediate compound (0.40 g) was used instead of the compound (13 g) synthesized in Example 1, and chloride acrylate (0.14 g) was used instead of chloride methacrylate (6.5 g), and that the amount of triethylamine was changed to 0.18 g instead of 12 g. The structure of Product 5 was confirmed by 1H-NMR. Table 1 shows optical characteristics and practical utility of Product 5.

Product 5

$^1$H-NMR (CDCl3; TMS): δ 2.21 (s, 6H), 3.81-3.91 (m, 2H), 4.10-4.19 (m, 2H), 5.78 (d, 1H), 6.36 (d, 1H), 6.40 (dd, 1H), 6.98 (s, 1H), 7.02 (s, 2H), 7.35-7.69 (m, 14H)

Example 6

A tetrahydrofuran solution (25 mL) of 2-(4-bromophenyl)-1,1-diphenyl ethylene (2.0 g) was cooled to −78° C., and n-butyllithium (2.6 M, 2.6 mL) was gradually dropped therein. The resulting mixture was stirred at the same temperature for 2 hours. After addition of 2,6-dimethylbenzaldehyde (0.65 g), the mixture was stirred for 12 hours while slowly warming to 25° C. After confirmation of the degree of reaction progress by TLC, the reaction was quenched with an aqueous solution of ammonium chloride, and the organic phase was extracted with ethyl acetate. The resulting organic phase was dried over anhydrous magnesium sulfate, concentrated, and purified by column chromatography.

Manganese dioxide (5 g) was added to a chloroform solution (30 mL) of the resulting intermediate compound, the mixture was stirred at 25° C. for 12 hours. After confirmation of the degree of reaction progress by TLC, the manganese dioxide was removed by filtration, and (2,6-dimethylphenyl)-[4-(2,2-diphenylvinyl)phenyl]methanone (6) (1.0 g, yield: 54%) was obtained by recrystallization as a light yellow liquid. The structure of Product 6 was confirmed by 1H-NMR. Table 1 shows optical characteristics and practical utility of Product 6.

Product 6

$^1$H-NMR (CDCl3; TMS): δ 2.09 (s, 6H), 6.98-7.34 (m, 16H), 7.55 (d, 2H)

Example 7

[4-(2,2-Diphenylvinyl)phenyl]-2-tolylmethanone (7) (1.1 g, yield: 60%) was obtained as a light yellow liquid by the same method described in Example 6 except that ortho-tolualdehyde (0.72 g) was used instead of 2,6-dimethylbenzaldehyde (0.65 g). The structure of Product 7 was confirmed by 1H-NMR. Table 1 shows optical characteristics and practical utility of Product 7.

Product 7

$^1$H-NMR (CDCl3; TMS): δ 2.40 (s, 3H), 7.01 (s, 1H), 7.25-7.68 (m, 18H)

Example 8

[4-(2,2-Diphenylvinyl)phenyl]-(2,4,6-trimethylphenyl)methanone (8) (1.4 g, yield: 63%) was obtained as a light yellow solid by the same method described in Example 6 except that 2,4,6-trimethylbenzaldehyde (0.78 g) was used instead of 2,6-dimethylbenzaldehyde (0.65 g). The structure of Product 8 was confirmed by 1H-NMR. Table 1 shows optical characteristics and practical utility of Product 8.

Product 8

$^1$H-NMR (CDCl3; TMS): δ 2.26 (s, 6H), 2.32 (s, 3H), 7.08 (s, 1H), 7.16-7.51 (m, 16H)

Example 9

[4-(2,2-Diphenylvinyl)phenyl]-(2-methylnaphthyl)methanone (9) (1.0 g, yield: 540) was obtained as a light yellow solid by the same method described in Example 6 except that 2-methyl-1-naphthylaldehyde (0.82 g) was used instead of 2,6-dimethylbenzaldehyde (0.65 g). The structure of Product 9 was confirmed by 1H-NMR. Table 1 shows optical characteristics and practical utility of Product 9.

Product 9

$^1$H-NMR (CDCl3; TMS): δ 2.27 (s, 3H), 7.08 (s, 1H), 7.15-7.64 (m, 20H)

Example 10

Synthesis Example 2

Synthesis process of 2-methoxymethoxy benzaldehyde

Salicylaldehyde (3 g) was slowly added to a N,N-dimethylformamide solution (50 mL) of sodium hydride (55%, 1.2 g) at 0° C. The mixture was stirred at the same temperature for 1 hour. Subsequently, chloromethylmethyl ether (2.9 g) was added thereto. After confirmation of the degree of reaction progress by TLC, the reaction was quenched with an aqueous solution of ammonium chloride. The organic layer was extracted with ethyl acetate and then was dried over anhydrous magnesium sulfate. The crude product obtained by concentrating the organic phase was purified by column chromatography to obtain 3.9 g (yield: 96%) of 2-methoxymethoxybenzaldehyde.

A tetrahydrofuran solution (30 mL) of the intermediate compound was prepared by the same method described in Example 6 except that 2-methoxymethoxybenzaldehyde (1.2 g) synthesized in the above-described Synthesis Example 2 was used instead of 2,6-dimethylbenzaldehyde (0.65 g). A 6 N hydrochloric acid solution (1 mL) was added to the tetrahydrofuran solution, and the mixture was stirred at 25° C. for 12 hours. After confirmation of the degree of reaction progress by TLC, the reaction was quenched with an aqueous solution of sodium hydrogen carbonate, and the organic phase was extracted with ethyl acetate. The resulting organic phase was dried over anhydrous magnesium sulfate, concentrated, and recrystallized to obtain 1.9 g (yield: 84%) of [4-(2,2-diphenylvinyl)phenyl]-(2-hydroxyphenyl)methanone (10) as yellow crystals. The structure of Product 10 was confirmed by $^1$H-NMR. Table 1 shows optical characteristics and practical utility of Product 10.

Product 10

$^1$H-NMR (CDCl3; TMS): δ 6.98 (d, 1H), 7.06 (s, 1H), 7.08 (d, 1H), 7.38-7.74 (m, 16H), 11.60 (s, 1H)

Example 11

2-[4-(2,2-Diphenylvinyl)benzoyl]phenyl methacrylate (11) (2.0 g, yield: 85%) was obtained as a light yellow liquid by the same method described in Example 2 except that the compound (2.0 g) synthesized in Example 10 was used instead of the compound (16.5 g) synthesized in Example 1 and that the amount of chloride methacrylate was changed to 0.66 g instead of 6.5 g, the amount of triethylamine was changed to 0.77 g instead of 12 g, and the volume of the chloroform solution was changed to 12 mL instead of 150 mL. The structure of Product 11 was confirmed by 1H-NMR. Table 1 shows optical characteristics and practical utility of Product 11.

Product 11

$^1$H-NMR (CDCl3; TMS): δ 1.81 (s, 3H), 5.55 (s, 1H), 5.97 (s, 1H), 6.97 (s, 1H), 7.05-7.55 (m, 18H)

Example 12

Synthesis Example 3

Synthesis process of 2-methoxymethoxy-5-methylbenzaldehyde

2-Methoxymethoxy-5-methylbenzaldehyde (3.3 g, yield: 90%) was obtained by the same method described in Synthesis Example 2 except that 5-methylsalicylaldehyde (2.8 g) was used instead of salicylaldehyde (3 g).

An intermediate compound was prepared by the same method described in Example 6 except that 2-methoxymethoxy-5-methylbenzaldehyde (1.3 g) synthesized in the above-described Synthesis Example 3 was used instead of 2,6-dimethylbenzaldehyde (0.65 g). A 6 N hydrochloric acid solution (1 mL) was added to a tetrahydrofuran solution (30 mL) of the intermediate compound, and the mixture was stirred at 25° C. for 12 hours. After confirmation of the degree of reaction progress by TLC, the reaction was quenched with an aqueous solution of sodium hydrogen carbonate, and the organic phase was extracted with ethyl acetate. The resulting organic phase was dried over anhydrous magnesium sulfate, concentrated, and recrystallized to obtain 2.0 g (yield: 84%) of [4-(2,2-diphenylvinyl)phenyl]-(2-hydroxy-5-methylphenyl)methanone (12) as white crystals. The structure of Product 12 was confirmed by 1H-NMR. Table 1 shows optical characteristics and practical utility of Product 12.

Product 12

$^1$H-NMR (CDCl3; TMS): δ 2.40 (s, 3H), 6.97 (s, 1H), 7.06 (d, 1H), 7.25-7.75 (m, 16H), 11.58 (s, 1H)

Example 13

2-[4-(2,2-Diphenylvinyl)-benzoyl]-4-methylphenyl methacrylate (13) (0.9 g, yield: 84%) was obtained as a light yellow solid by the same method described in Example 2 except that the compound (1.0 g) synthesized in Example 12 was used instead of the compound (16.5 g) synthesized in Example 1 and the amount of chloride methacrylate was changed to 0.3 g instead of 6.5 g, the amount of triethylamine was changed to 0.5 g instead of 12 g, and the volume of the chloroform solution was changed to 20 mL instead of 150 mL. The structure of Product 13 was confirmed by 1H-NMR. Table 1 shows optical characteristics and practical utility of Product 13.

Product 13

$^1$H-NMR (CDCl3; TMS): δ 1.90 (s, 3H), 2.41 (s, 3H), 5.60 (s, 1H), 6.14 (s, 1H), 6.97 (s, 1H), 7.17 (d, 1H), 7.25-7.75 (m, 16H)

Comparative Example 1

Biphenyl(2,6-dimethylphenyl)methanone (14) (1.4 g, yield: 76%) was obtained as white crystals by the same method described in Example 6 except that 4-bromobiphenyl (1.5 g) was used instead of 2-(4-bromophenyl)-1,1-diphenylethylene (2.0 g) and that the volume of n-butyllithium (2.6 M) was changed to 2.7 mL instead of 2.6 mL, and the amount of 2,6-dimethylbenzaldehyde was changed to 1.0 g instead of 0.65 g. The structure of Product 14 was confirmed by 1H-NMR. Table 1 shows optical characteristics and practical utility of Product 14.

Product 14

$^1$H-NMR (CDCl3; TMS): δ 2.16 (s, 6H), 7.09 (d, 2H), 7.23-7.48 (m, 8H), 7.87 (d, 2H)

Comparative Example 2

A tetrahydrofuran solution (2.0 mL) containing 0.32 g of magnesium and a small amount of iodide was cooled to 0° C., and a tetrahydrofuran solution (8.0 mL) of bromotriphenyl ethylene (3.0 g) was slowly dropped into the tetrahydrofuran solution over 1 hour. The resulting mixture was stirred at the same temperature for 1 hour, and then 2,6-dimethylbenzaldehyde (0.66 g) was added thereto. The mixture was stirred for 12 hours while warming to 25° C. After confirmation of the degree of reaction progress by TLC, the reaction was quenched with an aqueous solution of ammonium chloride, and the organic phase was extracted with ethyl acetate. The resulting organic phase was dried over anhydrous magnesium sulfate, concentrated, and purified by column chromatography. Dess-Martin periodinane (1.5 g) was added to a chloroform solution (30 mL) of the resulting intermediate compound at 0° C., the mixture was stirred for 2 hours. After confirmation of the degree of reaction progress by TLC, the reaction was quenched with water, and the organic phase was extracted with ethyl acetate.

The resulting organic phase was dried over anhydrous magnesium sulfate, concentrated, and purified by column chromatography to obtain 0.81 g (yield: 41%) of 1-(2,6-dimethylphenyl)2,3,3-triphenylpropenone (15) as yellow crystals. The structure of Product 15 was confirmed by 1H-NMR. Table 1 shows optical characteristics and practical utility of Product 15.

Product 15

$^1$H-NMR (CDCl3; TMS): δ 2.38 (s, 6H), 6.66 (d, 2H), 6.80-7.19 (m, 16H)

Comparative Example 3

A tetrahydrofuran solution (1.2 mL) containing 0.25 g of magnesium was cooled to 0° C., and a tetrahydrofuran solution (5.0 mL) of 2-bromoindene (1.0 g) was slowly dropped into the tetrahydrofuran solution. After completion of the dropping, the mixture was stirred at the same temperature for 1 hour, and then 2,6-dimethylbenzaldehyde (0.57 g) was added thereto. The mixture was stirred for 12 hours while warming to 25° C. After confirmation of the degree of reaction progress by TLC, the reaction was quenched with an aqueous solution of ammonium chloride, and the organic phase was extracted with ethyl acetate. The resulting organic phase was dried over anhydrous magnesium sulfate, concentrated, and purified by column chromatography.

Manganese dioxide (5 g) was added to a chloroform solution (30 mL) of the resulting intermediate compound, the mixture was stirred at 25° C. for 12 hours. After confirmation of the degree of reaction progress by TLC, the manganese dioxide was removed by filtration, and 0.42 g (yield: 400) of 2-(2,6-dimethylbenzoyl)indene (16) was obtained by recrystallization. The structure of Product 16 was confirmed by 1H-NMR. Table 1 shows optical characteristics and practical utility of Product 16.

Product 16

$^1$H-NMR (CDCl3; TMS): δ 2.21 (s, 6H), 3.85 (s, 2H), 7.07 (d, 2H), 7.20-7.26 (m, 2H), 7.33-7.41 (m, 2H), 7.47 (d, 1H), 7.58 (d, 1H)

Evaluation Method

The measurements shown in Table 1 were performed by the following methods.

Refractive indices were measured with an Abbe refractometer (Kalnew Co., Ltd.), and the Abbe number and the secondary dispersion characteristics were respectively calculated by the following equations:

Abbe number$[\nu d]=(nd-1)/(nF-nC)$

Secondary dispersion characteristics $[\theta g,F]=(ng-nF)/(nF-nC)$.

Transmittances were measured using films having a light path of 50 μm and with a spectrophotometer, U-4000 (a trade name), manufactured by Hitachi High-Technologies Corp. The transmittances are those at a wavelength of 430 nm.

The stability was evaluated after storage for two weeks in an atmosphere at 25° C., and one that was not deteriorated is shown by O, and one that was deteriorated is shown by x. Note that those having polymerizable substituents were judged in the presence of a small amount (1000 ppm or less) of a polymerization inhibitor. Those having optical characteristics belonging to the range B in FIG. 1 and a transmittance of 90% or more at 430 nm are shown by O in total evaluation, and others than those are shown by X in the total evaluation.

TABLE 1

|  |  | nd | vd | θg, F | Transmittance | Stability | Total evaluation |
|---|---|---|---|---|---|---|---|
| Example 1 | Product 1 | 1.64 | 14.35 | 0.856 | 94 | O | O |
| Example 2 | Product 2 | 1.64 | 14.79 | 0.843 | 93 | O | O |
| Example 3 | Product 3 | 1.64 | 17.72 | 0.845 | 93 | O | O |
| Example 4 | Product 4 | 1.63 | 18.02 | 0.805 | 95 | O | O |
| Example 5 | Product 5 | 1.63 | 18.11 | 0.807 | 95 | O | O |
| Example 6 | Product 6 | 1.66 | 13.13 | 0.861 | 92 | O | O |
| Example 7 | Product 7 | 1.67 | 13.02 | 0.871 | 93 | O | O |
| Example 8 | Product 8 | 1.65 | 13.25 | 0.859 | 94 | O | O |
| Example 9 | Product 9 | 1.71 | 12.87 | 0.881 | 93 | O | O |
| Example 10 | Product 10 | 1.66 | 13.33 | 0.861 | 90 | O | O |
| Example 11 | Product 11 | 1.64 | 14.43 | 0.853 | 94 | O | O |
| Example 12 | Product 12 | 1.65 | 13.51 | 0.859 | 90 | O | O |
| Example 13 | Product 13 | 1.64 | 13.58 | 0.852 | 94 | O | O |
| Comparative Example 1 | Product 14 | 1.64 | 18.27 | 0.684 | 97 | O | X |
| Comparative Example 2 | Product 15 | 1.64 | 18.03 | 0.774 | 23 | O | X |
| Comparative Example 3 | Product 16 | 1.62 | 17.30 | 0.698 | 35 | O | X |

Structural formulae of Products 1 to 16 are shown below.

Product 1
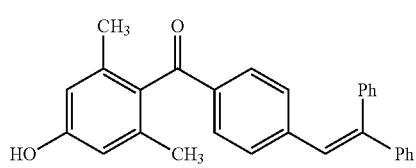

Product 2
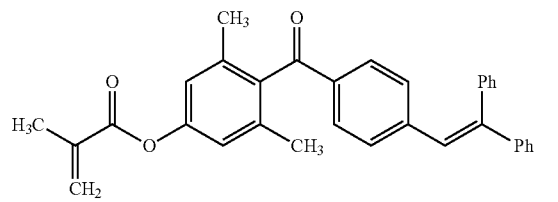

Product 3
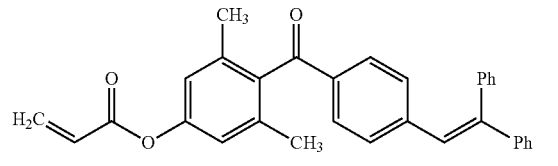

Product 4
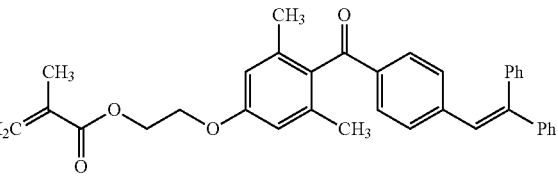

Product 5
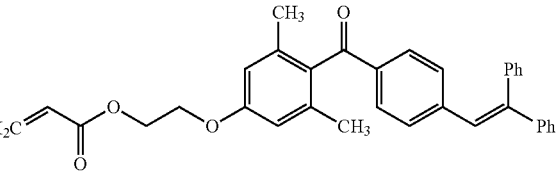

Product 6
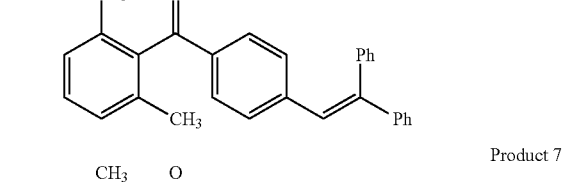

Product 7
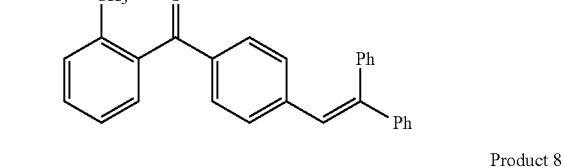

Product 8

Product 9
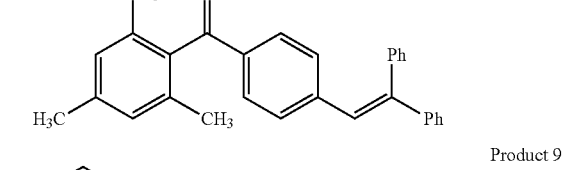

-continued

Product 10
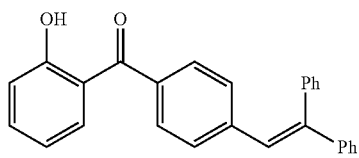

Product 11
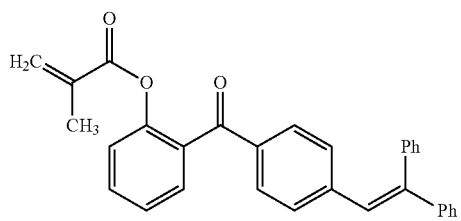

Product 12
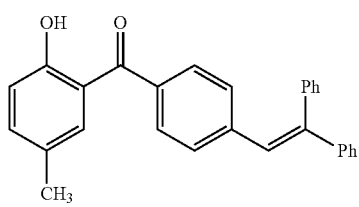

Product 13
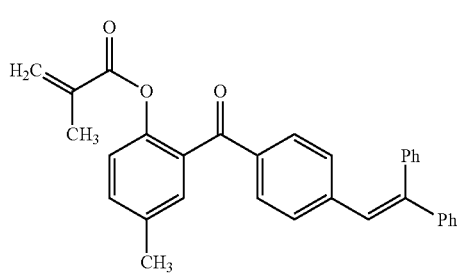

Product 14
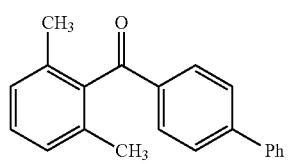

Product 15
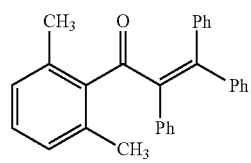

Product 16
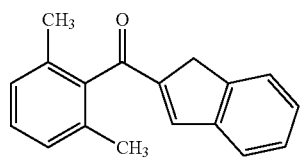

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-066988, filed Mar. 23, 2010, which is hereby incorporated by reference herein in its entirety.

The invention claimed is:

1. A compound corresponding to the following Formula (1):

Formula (1)

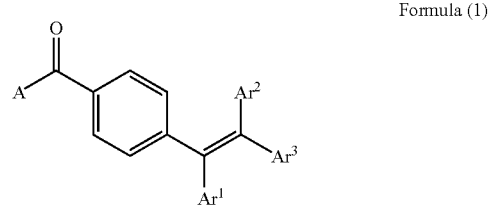

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ correspond to an aryl group optionally having a substituent; and wherein A has a structure corresponding to the following Formula (2):

Formula (2)

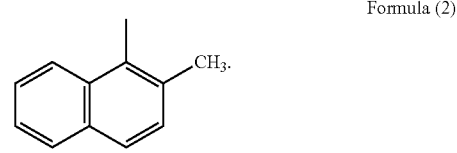

2. The compound according to claim 1, wherein $Ar^1$ is a hydrogen atom.

3. An optical material comprising a compound corresponding to the following Formula (1):

Formula (1)

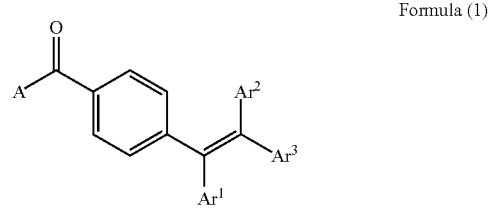

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ corresponds to an aryl group optionally having a substituent; and wherein A has a structure corresponding to the following Formula (2):

Formula (2)

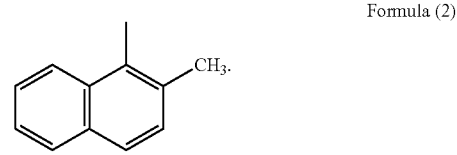

4. The optical material according to claim 3, wherein $Ar^1$ is a hydrogen atom.

5. A compound corresponding to the following Formula (1):

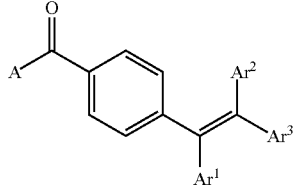

Formula (1)

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ correspond to an aryl group optionally having a substituent, and wherein A has a structure corresponding to the following Formula (3):

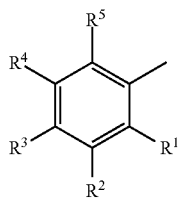

Formula (3)

wherein $R^1$ to $R^5$ in Formula (3) are:
- $R^1$ and $R^3$ are each Y, and $R^2$, $R^4$, and $R^5$ are hydrogen atoms;
- $R^1$ and $R^2$ are each Y, and $R^3$, $R^4$, and $R^5$ are hydrogen atoms;
- $R^1$ is Y, and $R^2$, $R^3$, $R^4$, and $R^5$ are hydrogen atoms;
- $R^1$ is Y, $R^2$, $R^3$, and $R^5$ are hydrogen atoms, and $R^4$ is a methyl group;
- $R^1$ and $R^5$ are methyl groups, $R^2$ and $R^4$ are hydrogen atoms, and $R^3$ is Y;
- $R^1$ is Y, $R^2$ and $R^4$ are tert-butyl groups, and $R^3$ and $R^5$ are hydrogen atoms;
- $R^1$, $R^3$, and $R^5$ are each Y, and $R^2$ and $R^4$ are hydrogen atoms;
- $R^1$, $R^2$, and $R^3$ are each Y, and $R^4$ and $R^5$ are hydrogen atoms; or
- $R^1$ is Y, $R^2$ is a methyl group, and $R^3$, $R^4$, and $R^5$ are hydrogen atoms, wherein Y corresponds to a hydroxyl group or a group having a structure corresponding to the following Formula (4):

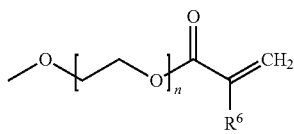

Formula (4)

$R^6$ corresponds to a hydrogen atom or a methyl group; and n is 0 or 1.

6. An optical material comprising a compound corresponding to the following Formula (1):

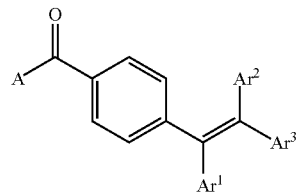

Formula (1)

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ corresponds to an aryl group optionally having a substituent; and wherein A has a structure corresponding to the following Formula (2):

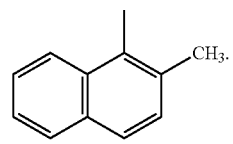

Formula (2)

7. A molded product comprising a material containing a polymer of a compound of Formula (1), or a mixture of the compound of Formula (1) and a resin:

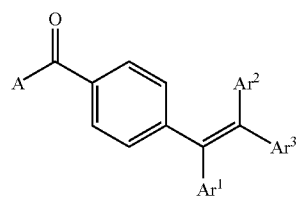

Formula (1)

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ corresponds to an aryl group optionally having a substituent; and wherein A has a structure corresponding to the following Formula (2):

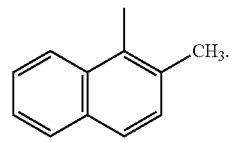

Formula (2)

8. The molded product according to claim 7, wherein $Ar^1$ is a hydrogen atom.

9. An optical element comprising the molded product defined in claim 7.

10. The optical element according to claim 9, wherein the optical element has the molded product between two glass substrates.

11. A molded product comprising a material containing a polymer of a compound of Formula (1), or a mixture of the compound of Formula (1) and a resin:

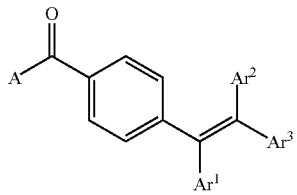

Formula (1)

in the formula, $Ar^1$ corresponds to a hydrogen atom or an aryl group optionally having a substituent; $Ar^2$ and $Ar^3$ each correspond to a hydrogen atom or an aryl group optionally having a substituent but at least one of $Ar^2$ and $Ar^3$ correspond to an aryl group optionally having a substituent, and wherein A has a structure corresponding to the following Formula (3):

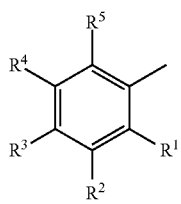

Formula (3)

wherein $R^1$ to $R^5$ in Formula (3) are:
$R^1$ and $R^3$ are each Y, and $R^2$, $R^4$, and $R^5$ are hydrogen atoms;
$R^1$ and $R^2$ are each Y, and $R^3$, $R^4$, and $R^5$ are hydrogen atoms;
$R^1$ is Y, and $R^2$, $R^3$, $R^4$, and $R^5$ are hydrogen atoms;
$R^1$ is Y, $R^2$, $R^3$, and $R^5$ are hydrogen atoms, and $R^4$ is a methyl group;
$R^1$ and $R^5$ are methyl groups, $R^2$ and $R^4$ are hydrogen atoms, and $R^3$ is Y;
$R^1$ is Y, $R^2$ and $R^4$ are tert-butyl groups, and $R^3$ and $R^5$ are hydrogen atoms;
$R^1$, $R^3$, and $R^5$ are each Y, and $R^2$ and $R^4$ are hydrogen atoms;
$R^1$, $R^2$, and $R^3$ are each Y, and $R^4$ and $R^5$ are hydrogen atoms; or
$R^1$ is Y, $R^2$ is a methyl group, and $R^3$, $R^4$, and $R^5$ are hydrogen atoms,
wherein Y corresponds to a hydroxyl group or a group having a structure corresponding to the following Formula (4):

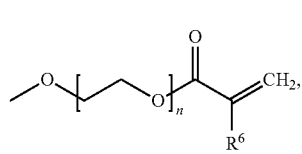

Formula (4)

$R^6$ corresponds to a hydrogen atom or a methyl group; and n is 0 or 1.

12. The molded product according to claim 10, wherein $Ar^1$ is a hydrogen atom.

13. An optical element comprising the molded product defined in claim 11.

14. The optical element according to claim 13, wherein the optical element has the molded product between two glass substrates.

* * * * *